United States Patent [19]
Brownlee

[11] Patent Number: 5,154,187
[45] Date of Patent: Oct. 13, 1992

[54] ABDOMINAL PRESSURE DIFFUSER

[75] Inventor: Merrel Brownlee, Lowellville, Ohio

[73] Assignee: Trumbull Land Co., Youngstown, Ohio

[21] Appl. No.: 790,422

[22] Filed: Nov. 12, 1991

[51] Int. Cl.5 ............................................. A61F 13/00
[52] U.S. Cl. .................... 128/888; 128/876; 128/889
[58] Field of Search .............. 128/96.1, 876, 870, 128/871, 869, 99.1, 102.1, 104.1, 105.1, 107.1, 78, 888, 889, 846

[56] References Cited

U.S. PATENT DOCUMENTS

| 1,378,317 | 5/1921 | Bobo | 128/104.1 |
| 1,720,439 | 7/1929 | Richardson | 128/891 |
| 2,367,690 | 1/1945 | Purdy | 128/888 |
| 2,520,436 | 8/1950 | Russell | 128/888 |
| 2,547,643 | 4/1951 | Hinkle | 128/102.1 |
| 2,663,020 | 12/1953 | Cushman | 128/889 |
| 3,274,996 | 9/1966 | Jewett | 128/78 |
| 3,976,066 | 8/1976 | McCartney | 128/889 |
| 4,000,737 | 1/1977 | Horn | 128/888 |
| 4,023,569 | 5/1977 | Warnecke et al. | 128/888 |
| 4,155,360 | 5/1979 | Erickson | 128/891 |
| 4,159,021 | 6/1979 | Casburn | 128/889 |
| 4,294,239 | 10/1981 | Oram | 128/96.1 |
| 4,926,883 | 5/1990 | Strock | 128/888 |
| 5,072,738 | 12/1991 | Wonder | 128/888 |

Primary Examiner—Robert A. Hafer
Assistant Examiner—David J. Kenealy
Attorney, Agent, or Firm—Harpman & Harpman

[57] ABSTRACT

An adjustable protective device for positioning on a human body, expanding the abdominal region so as to space a garment supporting the belt and/or a belt integrally formed with a garment from the abdominal area in the general area of the groin. The device is of a size spacing its cushioned ends substantially on either side of the groin area and is positioned between the human body and/or a garment such as an underear brief and a belt with respect to the abdominal area including the groin so as to permit the wearer to sit down with the belt in spaced relation to the body and allow the abdomen to move outwardly and prevent pressure on the abdomen and more particularly on the bladder and/or any healing surgical incision in that area such as a prostate, a bladder or urethra duct operation would cause.

5 Claims, 1 Drawing Sheet

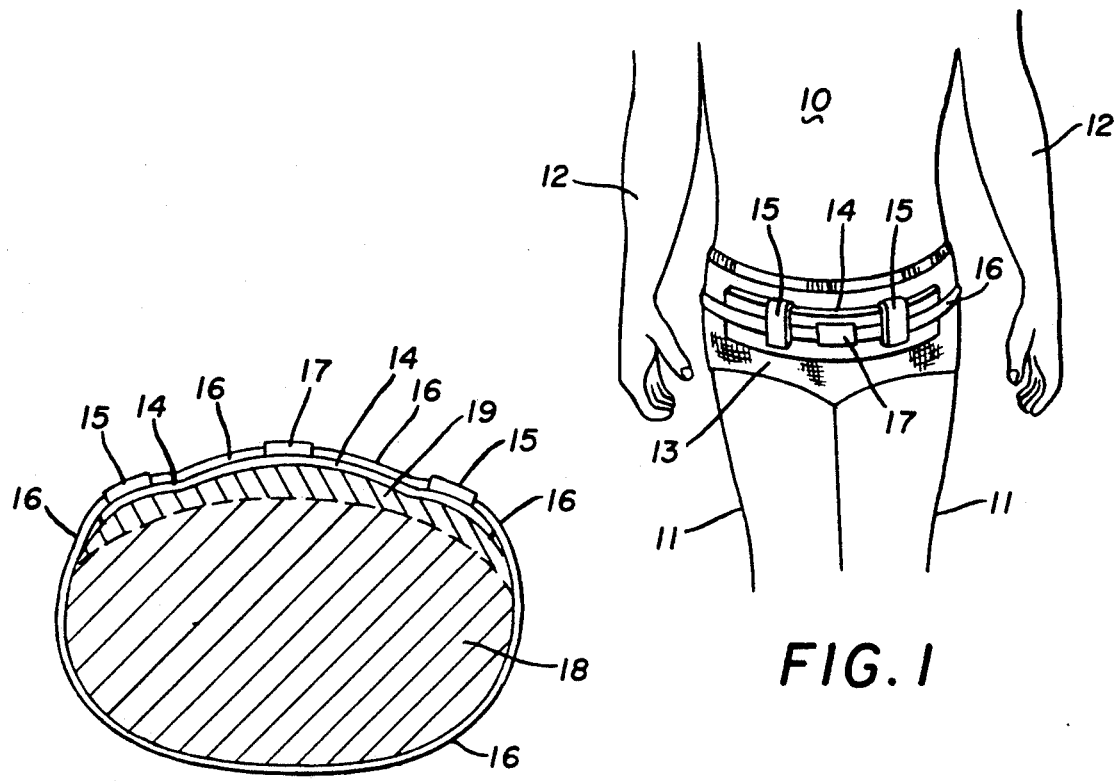
FIG. 4
FIG. 1
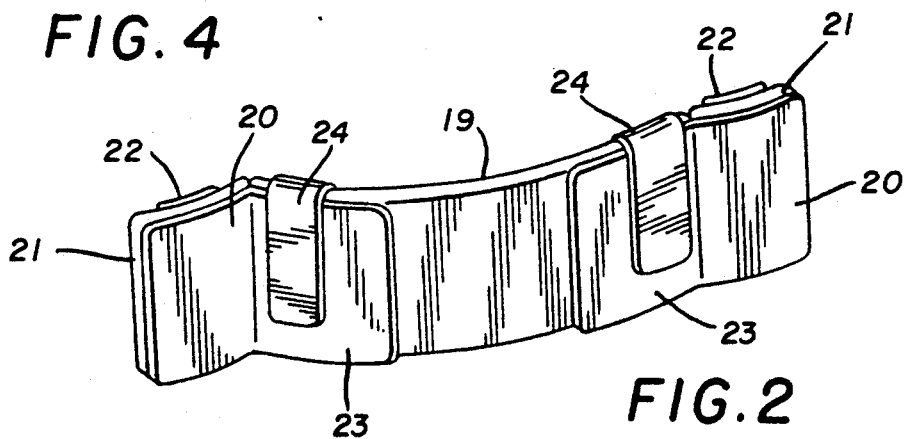
FIG. 2
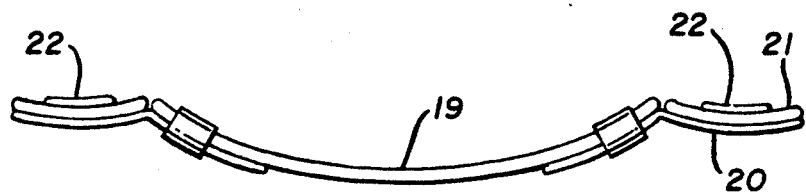
FIG. 3

ABDOMINAL PRESSURE DIFFUSER

BACKGROUND OF THE INVENTION

Major surgical procedures such as prostate operations for enlarging the urethra passageway therethrough and/or removal of cancerous areas therefrom or complete removal very frequently result in incisions into the body cavity and/or the prostate which are slow to heal and affect the ability to control urination when any pressure on the abdominal area including the groin is present such as occurs when a male sits down and his abdomen tends to protrude beyond its normal shape as restrained by a garment supporting belt or a belt integrally formed in a garment, etc.

The present invention is applicable to a female body for the same reasons with respect to bladder areas and areas adjacent thereto including the urethra and any similar or adjacent areas than an incision and/or removal or alteration of a body part results in incontinence due to pressure on the parts including the urethra and any normally present valves in the area.

The present invention provides a simple, inexpensive device which can be of a fixed size or adjustable which will effectively span the critical area and diffuse pressure that would otherwise be present from garments or garment holding belts so as to permit the abdominal area to expand normally when the wearer sits down and achieves this by spacing the garment holding belt or a belt integrally formed in a garment with respect to the critical area.

DESCRIPTION OF THE PRIOR ART

No prior art is known to applicant which discloses an abdominal pressure diffuser capable of eliminating pressure of garments of belts holding garments on the abdominal region of a human body to relieve pressure occurring when the wearer assumes a sitting position and the abdomen is restricted from moving outwardly with resulting stress incontinence as almost universally occurs in post operative prostatectomy cases.

U.S. Pat. No. 1,720,439 provides a belt supported groin protector which comprises a pair of depending arcuate members positioned over the legs of the wearer together with an apron-like device suspended thereover. A wound protector is seen in U.S. Pat. No. 2,520,436 in which a plurality of upwardly or outwardly bowed strips of material are held at their opposite ends by appropriate members to provide a bridging action over a wound on a human body. The construction is such that it cannot be applied to the abdominal area.

U.S. Pat. No. 2,663,020 illustrates a pneumatic injury pad with is incapable of being applied to the abdominal area in the manner of the present invention. U.S. Pat. No. 3,976,066 discloses a skin protective device which provides spaced means for holding a plurality of elevated rods over a wounded area.

U.S. Pat. No. 4,000,737 discloses a vertically positioned surgical incision shield which would be incapable of being applied to the abdominal area.

U.S. Pat. No. 4,023,569 discloses a device for the protection of wounds which is a shallow perforated bowl preferably elongated which could not be a applied to the abdominal area.

U.S. Pat. No. 4,159,021 discloses a chest incision protector which could not be applied to the abdominal area. U.S. Pat. No. 4,155,360 discloses a device to minimize pubic area irritation following surgery. While the device can be applied to the abdominal area, the device would be incapable of diffusing or relieving abdominal pressure in the manner of the present invention.

U.S. Pat. No. 4,926,883 shows an arched protective body appliance which is domed shaped rigid shield secured to a flexible compressible pad. It could not be applied to the abdominal area to relieve abdominal pressure when the wearer is seated and the abdomen moves forward and is restricted by a belt or garment.

SUMMARY OF THE INVENTION

An abdominal pressure diffuser of relatively rigid material takes the form of an elongated device having an outwardly bowed middle section with at least a 3" bow with respect to a horizontal line extending between the ends of the device and a pair of end portions defining the ends of the device which are themselves slightly bowed outwardly and provided with cushions and/or adhesive pads removably affixed thereto. Clips are affixed to the device at the outer sections of the central or middle bowed section and preferably inwardly of the end sections which can be engaged over a body encircling belt and buckle arrangement or garment band integrally with the garment so that the device is located between the belt or garment band and the body of the wearer. An alternate form of the invention provides forming the end sections as separate elements with inward extensions slidably engaged over the ends of the central section and movably secured thereto as for example by the clips which position the device on the belt or garment belt heretofore referred to.

DESCRIPTION OF THE DRAWINGS

FIG. 1 is illustrative of one embodiment of the invention in use;

FIG. 2 is a perspective view of a second embodiment of the invention;

FIG. 3 is a top plan view of the embodiment of the invention illustrated in FIG. 2; and FIG. 4 is a sectional view showing the device positioned over the abdominal area of a human body with cross hatching indicating the normal upright position of the body and secondary cross hatching indicating the position of the abdominal portion of the body extending outwardly when the body is seated rather than standing. A belt including a buckle is illustrated as being positioned on the device and extending around the sectional representation of the body.

DESCRIPTION OF THE PREFERRED EMBODIMENT

Referring to FIG. 1 of the drawings, the illustration of the device in use comprises a body 10 having portions of the legs 11 and arms 12 and an underwear garment, such as brief 13, positioned around the body 10 in the abdominal area as customary. An elongated outwardly curved body member 14 is illustrated spanning the abdominal area from points adjacent the sides thereof is provided with a pair of clips 15 which extend outwardly from the upper edge of the elongated body member 14 and then downwardly where they are illustrated as being positioned over a belt 16, with the usual belt buckle 17 which is used to support a garment such as a pair of trousers. It will be understood that the illustrated belt 16 can comprise an integral belt defining the upper end of a skirt which may or may not be adjustable or elastic and wherein the belt portion of the garment is positioned over the elongated outwardly curved body member 14 and the clips 15 are engaged thereover so as to retain it in desired position. It will be observed that in each example, the elongated outwardly curved body member 14 will hold the belt and buckle or the integral belt portion of a skirt in spaced relation to the abdominal area and any incision or healing wound in that area of the body and particularly in or adacent to the prostate or an area from which it has been removed or altered, the bladder, urethra and the vagina, uterus, bladder, etc. in a female body.

By referring now to FIG. 4 of the drawings, a cross section of a human body may be seen wherein the large oval shape 18 represents the position of this portion of the human body in the abdominal area when the body is in upright position as in standing or walking and an outwardly extending, forward extension 19 of the body is extended from the normal position 18 when the human body is in sitting position and the abdomen projects forwardly from its normal position when the body is upright. It is this expansion of the the abdominal area of the human body that is restricted by the conventional belt and buckle or belt formed integrally with a garment such as a skirt and which creates pressure on the bladder and any healing incision in the area thereof which ordinarily results in leakage from the bladder or incontinence as it is usually referred to.

In FIG. 4 of the drawings, cross hatchings 18 and 19 at different angles indicates these normal and extended portions of the body and the device of the invention, the abdominal pressure diffuser comprising the elongated outward curved body member 14 is illustrated with a belt 16 therearound including a buckle 17 and clips 15 on the elongated outwardly curved body member 14 engaged over the belt 16 so as to position the elongated outwardly extending body member 14 in a position holding the belt 16 and/or any comparable integral belt in a garment outwardly of the abdominal area so as to permit the normal expansion that occurs when the body is in seated position and the pressure which would otherwise result from the belt integrally formed in a garment is completely eliminated and incontinence as well as pain from any healing incisions or the like is eliminated.

It will occur to those skilled in the art that modifications can be made with respect to the embodiment of the invention hereinbefore described and one such desirable embodiment is illustrated in FIGS. 2 and 3 of the drawings and by referring to FIG. 2 it will be seen that the abdominal pressure diffuser includes an elongated outer curved body member 19 which is similar to the body member 14 of the first embodiment except that it is somewhat shorter and it is provided with a pair of end portions 20 which are provided with cushions 21 and if desired replaceable adhesive pads on the inner surfaces thereof and it will be observed that in the embodiment of the invention illustrated in FIGS. 2 and 3 of the drawings, the elongated outturned body member 19 is of a first known thickness and the end portions 20 are of a thickness considerably less than the known thickness of the body member 19 make up the difference in thickness with or without the optional removable adhesive attachment means.

It will also be observed that the device is provided with clips 24 which extend from the upper surface of the elongated outwardly curved body member 19 and extend downwardly over the inward extensions 23 of the end portions 20. They are preferably spring-like so that they can also accommodate and hold a belt not shown, comparable with the belt 16 hereinbefore described in connection with the first embodiment of the invention in FIGS. 1 and 4 or a belt integrally formed in a garment as also hereinbefore referred to.

Alternately, the inward extensions 23 may be slidably engaged in pockets or the like formed in the end portions of the elongated outwardly curved body member 19 as will occur to those skilled in the art.

In FIG. 3 of the drawings, a top plan view illustrates the relative thicknesses of the several parts and the length of the device in top plan in a typical abdominal pressure diffuser will be made in a length suitable for the wearer, for example 15" overall will fit a rather large human body, and a 10" or 12" overall length will fit a middle-sized human body or the like when the device is made in the first embodiment illustrated in FIGS. 1 and 4 hereinbefore described the overall length is accordingly controlled by the overall length of the elongated outwardly curved body member 14 while in the form of the second embodiment of the invention as seen in FIGS. 2 and 3 of the drawings the adjustably movable end portions 20 may be moved outwardly and inwardly by reason of the engagement of their inward extensions 23 with respect to the elongated outwardly curved body member 19 so that a device adjustable as to length results In such embodiments, an upward overall height of approximately 6" has been found to be desirable although it can be obviously increased for larger bodies if desired and the effective and therefore desirable length of the elongated outwardly curved body member 17 and/or 19 is approximately 12" in the larger size and in almost all shapes of the invention an outwardly curved area of at least 3" is defined by the body members 17 and 19 in order to permit at least this much expansion of the abdominal portion of the human body when the device is worn as hereinbefore described.

Those skilled in the art will observe that the abdominal pressure diffuser is patentably and functionally different with respect to the prior art disclosures comprising the U.S. patents listed on the accompanying list of prior art cited by applicant, Form PTO-1449, and having thus described my invention, what I claim is:

1. An abdominal pressure diffuser for a recent abdominal surgery incision site comprising in combination an elongated outwardly bowed member of a known height and length formed of a relatively rigid material, a pair of end portions of a height equal to said outwardly bowed member positioned in partial overlapping relationship on the outer surface of said elongated outwardly bowed member extending outwardly therefrom and supporting said elongated outwardly bowed member above said abdominal surgical incision site, clips on said elongated outwardly bowed member in spaced relation to one another and extending over the outer surface of said elongated outwardly bowed member in closely spaced relation thereto, each of said clips engaging one of said end portions for retaining the end portions in overlapping relationship with the elongated outwardly bowed member, and a belt engaged on said elongated outwardly bowed member beneath and between said clips for securing said abdominal pressure diffuser transversely of the abdominal surgical incision site so as to space said belt with respect to said abdominal surgical incision site and prevent pressure on the abdomen and more particularly on the bladder and any healing incision in that area.

2. The abdominal pressure diffuser for a recent abdominal surgical incision site comprising the combination set forth in claim 1 and wherein said offset end portions are angularly inclined in relation to said outer surface of said elongated outwardly bowed member to conform to the areas of the abdomen on which they are supported.

3. The abdominal pressure diffuser for a recent abdominal surgical incision site comprising the combination set forth in claim 2 and wherein said overlapping angularly inclined end portions are separate members adjustably engaged on said outer surface of said elongated outwardly bowed member so as to provide lengthwise adjustment of said abdominal pressure diffuser beyond said clips.

4. The abdominal pressure diffuser for a recent abdominal surgical incision site comprising the combination set forth in claim 1 and wherein said outwardly bowed member is of a known thickness and said end portions are of a thickness less than the known thickness of said outwardly bowed member and are movably engaged on said outer surface of said outwardly bowed member, cushion pads affixed to the end portions for engagement against the abdominal wall and removable adhesive pads affixed to said cusions for temporarily supporting said abdominal pressure diffuser while said belt is engaged on said elongated outwardly bowed member beneath said clips.

5. The abdominal pressure diffuser for recent abdominal surgical incision sites comprising the combination set forth in claim 1 and wherein said belt is annular.

* * * * *